United States Patent [19]

Nakayama et al.

[11] Patent Number: 5,041,375

[45] Date of Patent: Aug. 20, 1991

[54] METHOD OF PRODUCING CARNITINE

[75] Inventors: Kiyoshi Nakayama; Haruo Honda; Yukie Ogawa; Tetsuo Ohta; Tatsuya Ozawa, all of Kanagawa, Japan

[73] Assignee: Kyowa Hakko Kogyo Co., Ltd., Tokyo, Japan

[21] Appl. No.: 279,004

[22] Filed: Dec. 2, 1988

[30] Foreign Application Priority Data

Dec. 4, 1987 [JP] Japan ................................ 62-305830

[51] Int. Cl.$^5$ ...................... C12P 13/00; C12P 13/40; C12P 13/84
[52] U.S. Cl. .................................. 435/128; 435/136; 435/106; 435/280; 435/893
[58] Field of Search ............... 435/136, 106, 843, 822, 435/128, 280

[56] References Cited

U.S. PATENT DOCUMENTS

| | | | |
|---|---|---|---|
| 4,001,081 | 1/1977 | Commeyras | 435/129 |
| 4,366,250 | 12/1982 | Jallageas | 435/280 |
| 4,371,618 | 2/1983 | Cavazza | 435/128 |
| 4,636,471 | 1/1987 | Nakamura et al. | 435/280 |
| 4,642,290 | 2/1987 | Sih | 435/128 |

FOREIGN PATENT DOCUMENTS

| | | |
|---|---|---|
| 2603303 | 4/1988 | France . |
| 8504900 | 7/1985 | PCT Int'l Appl. . |
| 8607386 | 12/1986 | PCT Int'l Appl. . |
| 2195630 | 4/1988 | United Kingdom ................ 435/128 |

OTHER PUBLICATIONS

Fujita et al., *Chem. and Pharm. Bull.*, vol. 9, 1961 pp. 661–665.

Biotechnology and Bioengineering, vol. 26, pp. 911–915 (1984) "Chohinesterase-Catalyzed Resolution of D,L-Carnitine".

Applied and Environmental Microbiology, pp. 327–334 (1980) "Enzymatic Synthesis of L-Carnitine by Reduction of an Achiral Precursor: the Problem of Reduced Nicotinamide Adenine Dinucleotide Recycling".

*Primary Examiner*—Douglas W. Robinson
*Assistant Examiner*—Irene Marx
*Attorney, Agent, or Firm*—Sughrue, Mion, Zinn, Macpeak & Seas

[57] ABSTRACT

This invention relates to a method for producing carnitine comprising contacting, in a reaction medium, carnitinenitrile with (A) a nitrilase capable of hydrolyzing carnitinenitrile to form carnitine or (B) a microorganism containing said nitrilase.

6 Claims, No Drawings

METHOD OF PRODUCING CARNITINE

FIELD OF THE INVENTION

The present invention relates to a method for producing carnitine by hydrolyzing carnitinenitrile.

BACKGROUND OF THE INVENTION

Carnitine, one referred to as vitamin $B_T$, is a substance participating in the metabolism of fatty acids and the DL-form thereof has heretofore been used as a stomachic. Recently, attention has been directed particularly to L-form thereof.

L-Carnitine is a substance indispensable for the transportation of fatty acids to mitochondria and is used as a therapeutic agent for heat disorders, lipemia, etc., and also as a transfusion component of hyperalimentation fluids. It is also useful as an intermediate for the production of other useful substances such as acetyl-L-carnitine.

For a long time, a chemical synthetic method has been known for the production of carnitine. However, the synthetic method is disadvantageous, from the view-points of energy consumption and environmental pollution, since it involves heating and use of mineral acids, alkalis of toxic substances and since the resulting carnitine is in the DL-form. Further, L-carnitine has heretofore been produced by optically separating DL-carnitine, obtained by the chemical synthetic method, using a diastereomer method.

Recently, various biochemical approaches have been developed for the production of L-carnitine, for example, hydroxylation of 4-N-trimethylaminobutyric acid (*J. Biol. Chem.*, 256, 1247 (1981), reduction of 3-dehydrocarnitine (*Appl. Environm. Microbiol.*, 39, 329 (1980)), a method using 4-chloro-3-hydroxybutyric acid ester (JP-A-59-118093 (the term "JP-A" as used herein means an "unexamined published Japanese patent application")), a method using crotonobetain as a substrate (JP-A-59-183694 and JP-A-59-118093), a method in which DL-O-acylcarnitine is hydrolyzed with an esterase (*Biotechnol. Bioeng.*, 26, 911 (1984), etc.

These methods are disadvantageous from an industrial viewpoint since the starting materials used are expensive, the enzymes used are unstable and supply of expensive coenzymes is required. Although hydrolysis of carnitinenitrile with a mineral acid or the like has been known, biochemical hydrolysis of carnitinenitrile has not heretofore been known.

Further, to date, there have been no reports on a carnitinenitrile hydrolase which can be used in the production of intermediates for the synthesis of DL-carnitine.

SUMMARY OF THE INVENTION

An object of the present invention is to overcome the above-described disadvantages of the prior art and provide a method for producing L-carnitine biochemically.

Noticing the usefulness of carnitine, particularly its optically active isomer, L-carnitine, intensive investigation has been made on a biochemical method for producing carnitine directly from carnitinenitrile, the most efficient intermediate for the chemical synthesis of carnitine starting from epichlorohydrin. Further, it has been considered that if applicable to carnitinenitrile (an intermediate in the synthesis of carnitine), a method involving biochemical hydrolysis would be advantageous from the energy and environmental pollution viewpoint and become a commercially advantageous method of producing carnitine. Accordingly, not only have microorganisms from culture collections been investigated but also microorganisms newly isolated from natural sources have been investigated for an appropriate enzyme. As a result, a novel enzyme, nitrilase, more specifically carnitinenitrile hydrolase, has been found in the present invention which is useful in the biochemical hydrolysis of carnitinenitrile to obtain carnitine, and a method for producing this enzyme efficiently has been also found in the present invention.

Therefore, the present invention provides a method for producing carnitine comprising hydrolyzing carnitinenitrile by contacting, in a reaction medium, carnitinenitrile with (A) a nitrilase capable of hydrolyzing carnitinenitrile to form a carnitine or (B) a microorganism containing said nitrilase.

DETAILED DESCRIPTION OF THE INVENTION

The enzyme has an activity of hydrolyzing D-, L-, or DL-carnitinenitrile to form D-, L-, or DL-carnitine corresponding to the precursor used. When DL-carnitine is used as precursor, the yield of L-carnitine is more than that of D-carnitine.

The enzyme used in the method of the present invention is an enzyme capable of hydrolyzing carnitinenitrile to produce carnitine and is generally called nitrilase. The nitrilase is classified in the group of hydrolases which act on linear amid bonds (Class 3.5.5) according to the nomenclature of the international enzyme classification, and more specifically named as carnitinenitrile hydrolase. Heretofore, there has been no reports on nitrilases acting on those compounds having a trimethylamino group in the molecule, such as carnitinenitrile. Such enzymes have been found for the first time in the present invention.

Microorganisms which produce an enzyme capable of converting carnitinenitrile into carnitine can be selectively isolated based on the capability of producing carnitine from carnitinenitrile.

Specific examples of such microorganisms include bacteria belonging to the genus Corynebacterium, e.g., Corynebacterium sp. 6N-23 (FERM BP-2162), Corynebacterium sp. 11N-26 (FERM BP-2165), Corynebacterium sp. 6N-29 (FERM BP-2163), and Corynebacterium sp. 6N-49 (FERM BP-2164), which have been isolated by the present inventors. These strains are typical among the strains isolated by the present inventors as usable in the practice of the present invention and has been deposited at the Fermentation Research Institute, Agency of Industrial Science and Technology, ministry of International Trade and Industry, Japan of 1-3, Higashi 1-chome, Yatabe-machi, Tsukuba-gun, Ibaraki-ken, 305 Japan (hereinafter, referred to as "Bikoken") as the International Depositary under Budapest Treaty. The taxonomic properties of these strains are as described hereinbelow.

These isolated strains are all aerobic, non-sporing, Gram-positive coryneform bacteria. According to Bergey's Manual of Systematic Bacteriology, Vol. 2 (1986), they belong to irregular, nonsporing, gram-positive rods described in the Section 15 of the Bergey's Manual. Each strain contains mesodiaminopimelic acid in the cell wall and also contains mycoleic acids and therefore is considered to belong to the genus Corynebacterium.

The difficulty in classifying or identifying coryneform bacteria has so far been pointed out. The use of the chemical information-based classification in the above-cited recent classification manual has made it possible to distinguish bacterial strains from one another in a relatively clear manner as far as the genus is concerned. However, it is to be noted that there is still some difficulty in the present case. According to the chemistry-based classification, there are three candidate genera, namely Corynebacterium, Caseobacter and Rhodococcus, for the above-mentioned isolated strains since they contain meso-diaminopimelic acid in the cell wall and contains relatively short mycolic acids (as estimated by chromatography). In fact, the above Bergey's classification manual points out the difficulty in differentiating these three genera. While the Bergey's manual describes that the genus Rhodococcus shows nocardioforms, the above-mentioned isolated strains generally show coryneforms but show no nocardioforms. Therefore, the present inventors judged it possible to differentiate said isolated strains in that respect. For the genus Caseobacter, the above Bergey's manual described its strains as strictly aerobic and isolable from cheese, while mentioning only one species. On the other hand, most corynebacteria are facultatively anaerobic but some corynebacteria are aerobic. The genus Corynebacterium also includes strains isolated from soil samples. In view of the above, the present inventors identified the above-mentioned isolated strains as belonging to the genus Corynebacterium.

Hereinafter, the taxonomic characteristics of the isolated strains will be explained by separating the strains into several groups based on some common characteristics.

First, the characteristics which are common to all of the isolated strains are that they are gram-positive, aerobic, nonsporing coryneform rods, which show no acid fastness and have no motility. When they are cultured on bouillon agar medium, they form small colonies which have entire edges with elevation of convex form. The surface thereof is smooth. The luster is translucent. No diffusible pigments are produced. In a liquid bouillon medium they grow annularly on the surface and the medium becomes moderately turbid after growth.

Gelatin liquefaction does not occur. The VP test, indole synthesis and starch hydrolysis are negative for all of the strains. Utilization of an inorganic nitrogen source (nitrates and ammonium salts) is positive for all of the strains on glucose medium. Catalase, denitrification and urease all give positive results. Oxzidase gives negative results. They are judged to be fermentative based on acid formation in the O—F test performed by the Hugh-Leifson technique but no gas formation is observed. Utilization of citric acid is positive for all of the strains on Koser's medium. The litmus milk reaction produces little change; no reduction, coagulation or liquefaction occurs. As for the acid formation from sugars other than those shown in Table 1, the acid formation by the strains is positive for D-glucose, D-fructose, inositol, D-mannitol and glycerin but negative for D-galactose, sucrose, lactose, maltose and starch. Gas is not produced. They grow within the temperature range of 26° to 40° C. At 20° C., they grow only very slightly or do not grow at all. They all contain meso-diaminopimelic acid in the cell wall and contain relatively short mycolic acids intracellularly.

Table 1 below shows the additional taxonomic characteristics of the above-described strains grouped into Groups I, II, III and IV based on further common characteristics.

TABLE 1

| Characteristics | Group I | Group II | Group III | Group IV |
|---|---|---|---|---|
| Color of colonies on bouillon agar medium | Light yellow | White | Yellowish white | Flesh color |
| Cell size (μm) | 0.6–0.8x 0.8–2.0 | 0.6–1.2x 1.0–2.6 | 0.6–0.8x 0.9–2.8 | 0.5–0.7x 1.4–1.6 |
| Growing pH (optimum pH) | 6–10 (7–9) | 6–9 (6–8) | 6–8 (5–8) | 5–9 (5–8) |
| Reduction of nitrate | + | − | − | − |
| Formation of hydrogen sulfite | ± | ± | −** | ± |
| Acid formation from sugar | | | | |
| D-Xylose | − | + | + | + |
| D-Mannose | +* | − | − | + |
| L-Arabinose | − | + | − | + |
| Trehalose | + | − | + | − |
| D-Sorbitol | − | − | + | − |

*— in some strains.
**± on TSI medium (triple sugar iron agar) while, in some strains, + when tested by the lead acetate paper method.

Several strains having the above-mentioned properties have been isolated for each of the groups I to IV. Comparison of the properties of these strains with those of the species described in the above-cited classification Bergey's manual failed to establish complete agreement. Therefore, the present inventors identified their isolated strain as Corynebacterium sp. and deposited the following four strains at Bikoken: strain 6N-23, as typical representative of group I; strain 11N-26, as typical representative of group II; strain 6N-29, as typical representative of group III; and strain 6N-49, as typical representative of group IV.

The correspondence between the names of the strains deposited at Bikoken and their accession numbers are as listed below.

| Name of Strain | Accession Number |
|---|---|
| 6N-23 | FERM BP-2162 |
| 11N-26 | FERM BP-2165 |
| 6N-29 | FERM BP-2163 |
| 6N-49 | FERM BP-2164 |

These microorganisms can be wild strains or mutants. Strains containing genes coding for the nitrilase can also be used in the present invention.

The enzymes can be those extracted from the above-described microorganism cells or the culture broth. Immobilized enzymes and immobilized microorganisms containing the enzyme can also be employed as long as they exhibit nitrilase activity, more specifically carnitinenitrile hydrolase activity.

In order to obtain a culture containing a carnitinenitrile hydrolase activity by cultivating these microorganisms capable of producing this enzyme, usual cultivation methods can be used.

As to the fermentation medium employed in the present process for culturing the microorganism, any synthetic or natural medium can be employed, so long as it contains a proper carbon source, a nitrogen source, inorganic materials, and trace amounts of nutrients necessary for the specific microorganism.

Any carbon source and nitrogen source can be used in the medium, so long as they can be utilized by the microorganism. For example, carbohydrates such as glucose, fructose, sucrose, maltose, mannose, etc.; sugar alcohols such as sorbitol, mannitol; glycerol; starch; starch hydrolyzate liquor; molasses; etc. may be used. Further, various organic acids such as pyruvic acid, lactic acid, acetic acid, fumaric acid, gluconic acid, etc. and lower alcohols such as methanol, ethanol, glycols such as ethylene glycol, hydrocarbons such as ethane, propane, butane, n-paraffine, kelosene, etc. may also be used.

As a nitrogen source, the following substances are appropriate ammonia; various inorganic and organic ammonium salts such as ammonium chloride, ammonium sulfate, ammonium carbonate, ammonium phosphate, ammonium nitrate, ammonium acetate, etc.; urea and other nitrogen-containing materials; and nitrogenous organic materials such as peptone, NZ-amine, meat extract, yeast extract, corn steep liquor, casein hydrolyzate, fish meal or its digested product, chrysalis hydrolyzate, etc.

As inorganic materials, monopotassium dihydrogen phosphate, dipotassium monohydrogen phosphate, magnesium sulfate, sodium chloride, ferrous sulfate, manganese sulfate, calcium carbonate, etc., may be used.

If other nutrients are necessary for the growth of the microorganisms, they must, of course, be present in the medium. However, it is not necessary that they be separately added to the medium so long as they are supplied to the medium together with other medium components as described above. That is, certain natural ingredients may adequately supply the specific growth promoting factors.

Culturing is carried out under aerobic conditions such as by shaking or aeration-agitation. Suitable culturing temperature is usually 20° to 40° C. It is desirable to keep the pH of the medium around neutrality throughout culturing in order to obtain a high yield, but these temperature and pH conditions are not essential for the practice of the present invention. Culturing is usually carried out for 1 to 7 days.

After the completion of the culturing, the resultant culture broth is subjected to centrifugation, filtration or the like to obtain the microbial cells. The microbial cells as they are or the cells disrupted by suitable means such as ultrasonic disintegrator, etc. are used.

It is to be noted, however, that cultures having a high level of nitrilase activity can be obtained when the microorganisms are grown on a medium containing carnitinenitrile, which is the substrate in the practice of the invention. Further, both solids medium and liquid medium can be used in the present invention.

Of course, carnitinenitrile can be used in the form of a physiologically acceptable salt thereof, e.g., chloride and carnitine can be obtained in the form of a physiologically acceptable salt thereof, e.g., chloride or sulfate.

The microorganism cells having a nitrilase activity or enzyme preparation derived therefrom thus obtained can be contacted with the substrate (carnitinenitrile) by adding the enzyme preparation in a solution containing the substrate and incubating the reaction mixture until the reaction proceeds or by adding the substrate in a culture broth of the microorganism followed by incubation for reaction. Alternatively, the enzyme can be contacted with the substrate in the form of enzyme preparation or cells separated from a culture broth of the microorganism of the present invention, physicochemically or biochemically treated cells such as washed cells, lyophilized cells and acetone-dried cells, extract solution, purified preparations, immobilized preparations, etc.

The concentration of the substrate varies depending on whether a batch system or a continuous system is used. In the batch system, it ranges generally from about 0.1 to 30%, preferably from about 0.5 to 10%, by weight based on the weight of the reaction medium. In the continuous system, slightly lower ranges of the concentration, namely 0.05 to 20% by weight, are preferred.

The reaction can be carried out usually at about 5° to 60° C., preferably about 25° to 50° C., at a pH about 4 to 10, preferably at a pH about 6 to 8. The reaction time varies depending on the means of standing, stirring, flowing down through the column containing the immobilized enzyme, etc., or the form or activity of the enzyme but usually in a batch system it ranges from about 1 to 150 hours.

The process of the reaction can be monitored by monitoring the generation of carnitine using thin layer chromatography or by analysis of the generation of L-carnitine according to Pearson's enzyme method (D. J. Pearson et al., *Method in Enzymology*, vol. 14, 612 (1969)). The proportion of L-form/D-form in the total carnitine (L-form+D-form) or the optical purity can be determined by separating carnitine from the reaction mixture using silica gel chromatography, converting carnitine into carnitineamide of L-phenylalanine, measuring the areas of L-carnitineamide of L-phenyl-alanine and of D-carnitineamide of L-phenylalanine and calculating the ratio of the areas by high performance liquid chromatography. After completion of the reaction, the reaction mixture is passed through a column charged with an ion exchange resin, followed by elution, for example, with dilute hydrochloric acid and concentrated to recover L-carnitine chloride.

Thus, the invention provides a method of producing carnitine which comprises bringing carnitinenitrile, which can be synthesized with ease and at low costs, into contact with an enzyme (a kind of nitrilase) capable of hydrolyzing said nitrile to carnitine, said enzyme being used as such or in the form of an enzyme preparation, a biological preparation (microorganism, cells), an immobilized enzyme or an immobilized biological preparation.

According to the method of the present invention, the reaction can proceed under mild conditions, i.e., at room temperature and in the vicinity of neutral pH range, which is advantageous as compared with the conventional methods from the viewpoints of reduced energy consumption and prevention of environmental pollution. In contrast to the conventional biochemical methods using a compound derived from carnitine as a starting compound, the present invention enables one to produce optically active carnitine from optically inactive DL-carnitinenitrile which is an intermediate for the chemical synthesis of carnitine.

Hereinafter, the present invention will be described in greater detail with reference to examples which should by no means be construed as limiting the present invention thereto.

In the following examples all percentages are by weight unless otherwise indicated.

EXAMPLE 1

The bacterial strains shown in Table 2 were respectively inoculated into 30 ml of a sterilized medium (pH 7.2) containing 0.5% glucose, 0.25% peptone, 0.15% meat extract, 0.15% yeast extract, 0.125% NaCl and 1.0% DL-carnitinenitrile chloride as placed in a 300-ml erlenmeyer flask. After culturing 72 hours at 26° C., bacterial cells were collected by centrifugation. The cells were suspended in water, again collected by centrifugation and added to 100 mM sodium phosphate-sodium hydroxide buffer (pH 7.0) containing DL-carnitinenitrile chloride to the original cell concentration. At the same time, the concentration of DL-carnitinenitrile chloride was adjusted to 5%. A 50-ml portion of the mixture was placed in a 300-ml erlenmeyer flask and incubated stationarily at 26° C. for 72 hours, whereupon levo-rotatory (i.e., optically active) carnitine was formed in the reaction mixture. The thus-obtained L-carnitine concentrations as determined by the enzymatic method and the L-carnitine content of the product carnitine (percent proportion of L-form) were as shown below in Table 2.

TABLE 2

| Strain | Yield of L-carnitine (mg/ml) | Proportion of L-form in product carnitine (%) |
|---|---|---|
| 6N-23 | 4.5 | 78.1 |
| 11N-26 | 8.0 | 60.2 |
| 6N-29 | 14.1 | 67.8 |
| 6N-49 | 4.2 | 68.4 |

EXAMPLE 2

The same procedures as in Example 1 were repeated except that the strain 6N-49 was used as the microorganism and the culture medium containing 1% glucose, 0.1% NH$_4$Cl, 0.5% peptone, 0.5% NaCl, 0.75% K$_2$HPO$_4$, 0.25% KH$_2$PO$_4$, 0.05% MgSO$_4$.7H$_2$O, 0.01% FeSO$_4$.7H$_2$O and 1% DL-carnitinenitrile chloride (pH 7.2) was used. After the 72-hour reaction period, levorotatory carnitine was formed in the reaction mixture in an L-carnitine concentration of 18.1 mg/ml. The proportion of L-carnitine in the product carnitine was 60.5%. When the reaction period was prolonged to 120 hours, the yield of L-carnitine was 22.17 mg/ml.

The reaction mixture after 120 hours of reaction was applied to a strongly acidic cation exchange resin (sodium salt form) column for causing carnitine and carnitinenitrile to be adsorbed thereon. Then, the elution was performed by passing a diluted solution of ammonium acetate through the column for separation of carnitine from carnitinenitrile. Levo-rotatory carnitine was recovered by concentrating the carnitine fraction obtained, adding alcohol to the concentrate and cooling the resulting mixture.

EXAMPLE 3

The same procedure as in Example 1 were repeated except that the strain 6N-49 was used as the microorganism and the culture medium containing 3% glycerin, 0.5% peptone, 0.3% meat extract, 0.3% yeast extract, 0.25% NaCl (pH 7.2) was used. After 48 hours of reaction, the yield of L-carnitine was 24.4 mg/ml.

EXAMPLE 4

Cells of the strain 6N-49 obtained by cultivating the microorganism in the same manner as in Example 1 were suspended in physiological saline in a density of 200 mg/ml and 10 ml of the suspension was mixed with 10 ml of a 4% sodium alginate solution. The resulting mixture was proportionwise added to a 15% calcium chloride solution to obtain particulate immobilized cells. The total amount of the immobilized cells were added to 20 ml of a phosphate buffer solution (pH 7.0) containing 1% DL-carnitinenitrile chloride and allowed to stand at 30° C. for 16 hours for the reaction. As the result, 1.6 mg/ml of L-carnitine hydrochloride was formed.

As detailedly described hereinabove, the present invention provides a commercial method of producing carnitine, in particular optically active carnitine, preferably L-carnitine, in good yield which comprises bringing DL-carnitinenitrile, which is an intermediate in the synthesis of carnitine and can be synthesized at low costs, into contact with a specific microorganism or the enzyme produced by said microorganism.

EXAMPLE 5

The strain 6N-23 was inoculated into a sterilized medium (pH 7.2) containing 1% glucose, 0.5% peptone, 0.3% meat extract, 0.3% yeast extract, 0.25% NaCl and 1% L-carnitinenitrile chloride as an inducer of enzyme. After shake culturing at 26° C. for 72 hours at 220 r.p.m., bacterial cells were collected by centrifugation. The cells were suspended in water, again collected by centrifugation and added to 100 mM sodium phosphate-sodium hydroxide buffer (pH 7.0) containing the substrates shown in Table 3 to the original cell concentration. At the same time, the concentration of the substrates was adjusted to 5%. A 50-ml portion of the mixture was placed in a 300-ml erlenmeyer flask and incubated stationarily at 26° C. for 96 hours, whereupon the products shown in Table 3 were formed in the reaction mixture in a concentration shown in Table 3.

TABLE 3

| Substrate | Reaction Product | Concentration of Product (as chloride) (mg/ml) |
|---|---|---|
| L-carnitinenitrile chloride | L-carnitine | 55.9 |
|  | D-carnitine | 0 |
| D-carnitinenitrile chloride | L-carnitine | 0 |
|  | D-carnitine | 46.2 |
| DL-carnitinenitrile chloride | L-carnitine | 22.9 |
|  | D-carnitine | 10.7 |

EXAMPLE 6

The same procedures as in Example 5 were repeated except the D-carnitinenitrile chloride in place of L-carnitinenitrile chloride was used as an inducer to be contained in the culture medium.

The results are shown in Table 4.

TABLE 4

| Substrate | Reaction Product | Concentration of Product (as chloride) (mg/ml) |
|---|---|---|
| L-carnitinenitrile chloride | L-carnitine | 54.4 |
|  | D-carnitine | 0 |
| D-carnitinenitrile chloride | L-carnitine | 0 |
|  | D-carnitine | 35.8 |
| DL-carnitinenitrile chloride | L-carnitine | 27.4 |
|  | D-carnitine | 11.8 |

The calnitinenitrile-hydrolyzing activity of the bacterial cells cultured using a medium containing no inducer of enzyme is remarkably low, and the enzyme responsible for the reaction is an enzyme induced from carnitinenitrile. Further, its enzymatic activity do not act on carnitineamide.

While the invention has been described in detail and with reference to specific embodiments thereof, it will be apparent to one skilled in the art that various changes and modifications can be made therein without departing from the spirit and scope thereof.

What is claimed is:

1. A method for producing carnitine which comprises culturing in a nutrient medium a strain selected from the group consisting of Corynebacterium sp. FERM BP-2162, Corynebacterium sp. FERM BP-2165, Corynebacterium sp. FERM BP-2163 and Corynebacterium sp. FERM BP-2164 in the presence of carnitinenitrile or a salt thereof to obtain microbial cells and hydrolyzing carnitinenitrile or a salt thereof by contacting in a reaction medium carnitinenitrile or the salt thereof with said microbial cells.

2. The method as claimed in claim 1, wherein the product carnitine is in the optically active form.

3. The method as claimed in claim 1, wherein said carnitinenitrile is DL-carnitinenitrile and said carnitine is L-carnitine.

4. The method as claimed in claim 1, wherein said carnitinenitrile is DL-carnitinenitrile and said carnitine is D-carnitine.

5. The method as claimed in claim 1, wherein said carnitinenitrile is L-carnitinenitrile and said carnitine is L-carnitine.

6. The method as claimed in claim 1, wherein said carnitinenitrile is D-carnitinenitrile and said carnitine is D-carnitine.

* * * * *